United States Patent [19]

Berg

[11] Patent Number: 4,880,505

[45] Date of Patent: Nov. 14, 1989

[54] SEPARATION OF M-DIISOPROPYLBENZENE FROM P-DIISOPROPYLBENZENE BY AZEOTROPIC DISTILLATION WITH ESTERS

[75] Inventor: Lloyd Berg, 1314 South Third Ave., Bozeman, Mont. 59715

[73] Assignee: Lloyd Berg, Bozeman, Mont.

[21] Appl. No.: 275,589

[22] Filed: Nov. 23, 1988

[51] Int. Cl.$^4$ ............................ B01D 3/38; C07C 7/06
[52] U.S. Cl. ........................................ 203/60; 203/64; 585/866
[58] Field of Search ............................ 203/60, 63, 64; 585/804, 808, 807, 866

[56] References Cited

U.S. PATENT DOCUMENTS

| 2,398,689 | 4/1946 | Bloomer | 203/46 |
| 2,461,993 | 2/1949 | McKinnis | 203/62 |
| 2,805,258 | 9/1957 | Boodman et al. | 585/839 |
| 2,840,621 | 6/1958 | Corson et al. | 585/839 |
| 3,222,349 | 12/1965 | Holder | 585/804 |
| 4,128,594 | 12/1978 | Westernacher | 585/806 |

FOREIGN PATENT DOCUMENTS

| 49-47326 | 5/1975 | Japan | 585/866 |
| 50-70324 | 6/1975 | Japan | 585/864 |

Primary Examiner—Wilbur Bascomb

[57] ABSTRACT

Meta and para-diisopropylbenzenes cannot be easily separated from each other by distsillation because of the closeness of their vapor pressures. m-Diisopropylbenzene can be readily removed from p-diisopropylbenzene by azeotropic distillation using certain esters. Typical effective azeotropic distillation agents are methyl benzoate and diethylene glycol ethyl ether acetate.

9 Claims, No Drawings 4,880,505

SEPARATION OF M-DIISOPROPYLBENZENE FROM P-DIISOPROPYLBENZENE BY AZEOTROPIC DISTILLATION WITH ESTERS

This application is relates to co-pending application Ser. No. 07/270,200 filed on Nov. 14, 1988 related to the same separation of m-diisopropylbenzene from p-diisopropylbenzene using different agents.

FIELD OF THE INVENTION

This invention relates to a method for separating m-diisopropylbenzene from p-diisopropylbenzene using certain esters as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates or effect the same separation or make possible a greater degree of separation with the same number of plates. The azeotrope forming agent is introduced with the feed to a continous column. The azeotrope forming agent and the more volatile component are taken off as overhead product and the less volatile compound comess off as bottoms product. The usual methods of separating the azeotrope former from the more volatile component are cooling and phase separation or solvent extraction.

In the manufacture of cumene, also called isopropylbenzene, by the alkylation of benzene with propylene, the most prevalent by-products are the diisopropylbenzenes with the meta and para isomers comprising most of the by-product. m-Diisopropylbenzene (m-DIPB) boils at 203.2° C. m-Diisopropylbenzene (p-DIPB) boils at 210.3° C. and these two have a relative volatility of 1.14. The difficulty of separating these two by rectification can be shown by the data in Table 1.

TABLE 1

| Plates Required To Effect Separation In 99% Purity | | |
|---|---|---|
| Relative Volatility | Theoretical Plates | Actual Plates, 75% Efficiency |
| 1.14 | 71 | 95 |
| 1.22 | 47 | 63 |
| 1.25 | 41 | 55 |
| 1.29 | 36 | 48 |

Table 1 shows that rectification of m-DIPB from p-DIPB in 99% purity requires 95 actual plates. Using azeotropic distillation with an agent yielding a relative volatility of 1.29 would require only 48 actual plates. Thus azeotropic distillation would be an attractive method of effecting the separation of these isomers if agents can be found that (1) will increase the relative volatility of m-DIPB to p-DIPB and (2) are easy to recover from the p-DIPB.

Azeotropic distillation typically requires the addition of about as much agent as m-DIPB to be boiled up in the column which increases the heat requirement as well as somewhat larger diameter plates to accomodate the increase of liquid and vapor in the column. In addition, a solvent extraction column is usually provided to recover and recycle the azeotrope forming agent.

OBJECTIVE OF THE INVENTION

The objective of this invention is to provide a process or method of azeotropic distillation that will enhance the relative volatility of m-DIPB from p-DIPB in their separation in a rectification column. It is a further object of this invention to identify organic compounds which in addition to the above constraints, are stable, can be separated from m-DIPB by solvent extraction and can be recycled to the azeotropic distillation and reused with little decomposition.

SUMMARY OF THE INVENTION

The objects of this invention are provided by a process for separating m-DIPB from m-DIPB which entails the use of certain esters in an azeotropic distillation process.

DETAILED DESCRIPTION OF THE INVENTION

I have discovered that certain esters will effectively enhance the relative volatility of m-DIPB from p-DIPB and permit the separation of m-DIPB from p-DIPB by rectification when employed as the agent in azeotropic distillation. Table 2 lists the esters that I have found to be effective.

TABLE 2

| Effective Azeotrope Forming Agents - Esters | | |
|---|---|---|
| Compound | Azeotrope, B.P., °C. | Relative Volatility |
| Methyl benzoate | 192 | 1.29 |
| Ethyl benzoate | 199 | 1.27 |
| Dimethyl succinate | 188 | 1.26 |
| Diethyl oxalate | 179 | 1.25 |
| Diethylene glycol ethyl ether acetate | 198 | 1.24 |
| Diethyl malonate | 189 | 1.23 |
| Hexylene glycol diacetate | 179 | 1.23 |
| Dipropylene glycol methyl ether acetate | 196 | 1.20 |

TABLE 3

| Ineffective Esters | |
|---|---|
| Compound | Relative Volatility |
| Methyl phenyl acetate | 0.8 |
| Benzyl acetate | 1.08 |
| Ethylene glycol butyl ether acetate | No azeo. |
| Ethylene glycol ethyl ether acetate | No azeo. |
| Hexyl acetate | No azeo. |
| Diethyl succinate | 1.18 |
| Butyl butyrate | No azeo. |
| Diethyl maleate | 1.13 |

Table 3 lists some esters found to be ineffective. The data in Tables 2 and 3 were obtained in a vapor-liquid equilibrium still. In each case, the starting material was a mixture containing 50% ester, 25% m-DIPB and 25% p-DIPB. The boiling points of the azeotropes at 640 mm. Hg are shown. The relative volatilities are listed for each of the esters.

The esters which are effective are methyl benzoate, ethyl benzoate, dimethyl succinate, diethyl oxalate, diethyl malonate, hexylene glycol diacetate, diethylene glycol ethyl ether acetate and dipropylene glycol methyl ether acetate. The data in Table 2 indicates that one part of methyl benzoate mixed with one part of m-DIPB-p-DIPB mixture gives a relative volatility of 1.29.

THE USEFULNESS OF THE INVENTION

The usefulness or utility of this invention can be demonstrated by referred to Tables 1, 2 and 3. All of the successful azeotropic agents show that m-DIPB can be separated from p-DIPB by means of distillation in a rectification column and that the ease of separation as measured by relative volatility is considerable. Without these azeotropic agents, only a slight improvement will occur in a rectification column.

WORKING EXAMPLES

Example 1

Forty grams of m-DIPB-p-DIPB mixture and 40 grams of methyl benzoate were charged to an Othmer type vapor-liquid equilibrium still and refluxed for ten hours. Analysis by gas chromatography gave a vapor composition of 68.6% m-DIPB, 31.4% p-DIPB; a liquid composition of 61.5% p-DIPB, 38.5% p-DIPB. This indicates a relative volatility of m-DIPB to p-DIPB of 1.29.

Example 2

Forty grams of m-DIPB-p-DIPB mixture and 40 grams of diethylene glycol ethyl ether acetate were charged to the vapor-liquid equilibrium still and refluxed for five hours. Analysis indicated a vapor composition of 66.7% m-DIPB, 33.3% p-DIPB; a liquid composition of 61.7% m-DIPB, 38.2% p-DIPB which is a relative volatility of 1.24.

Example 3

A two foot long rectification column packed with Berl saddles was calibrated with m-DIPB and p-DIPB which possesses a relative volatility of 1.14 and found to have 2.3 theoretical plates. A solution comprising 80 grams of m-DIPB, 20 grams of p-DIPB and 20 grams of methyl benzoate was placed in the stillpot and heated. After one hour of refluxing at total reflux, analysis was made by gas chromatography. The overhead composition was 72% m-DIPB, 28% p-DIPB and the stillpot analysis was 59% m-DIPB, 41% p-DIPB. Using these compositions in the Fenske equation with the theoretical plates in the column being 2.3, gave an average relative volatility of 1.29 for each theoretical plate.

I claim:

1. A method for recovering m-diisopropylbenzene from a mixture of m-diisopropylbenzene and p-diisopropylbenzene which comprises distilling a mixture of m-diisopropylbenzene and p-diisopropylbenzene in a rectification column in the presence of an azeotrope forming agent, recovering the m-diisopropylbenzene and the azeotrope forming agent as overhead product, obtaining the p-diisopropylbenzene from the stillpot, wherein said azeotrope forming agent is an ester which forms a minimum boiling azeotrope with m-diisopropylbenzene, said azeotrope having a volatility relative to p-diisopropylbenzene in the range of 1.20 to 1.29.

2. The method of claim 1 in which the azeotrope forming ester is methyl benzoate.

3. The method of claim 1 in which the azeotrope forming ester is ethyl benzoate.

4. The method of claim 1 in which the azeotrope forming ester is dimethyl succinate.

5. The method of claim 1 in which the azeotrope forming ester is diethyl oxalate.

6. The method of claim 1 in which the azeotrope forming ester is diethyl malonate.

7. The method of claim 1 in which the azeotrope forming ester is hexylene glycol diacetate.

8. The method of claim 1 in which the azeotrope forming ester is diethylene glycol ethyl ether acetate.

9. The method of claim 1 in which the azeotrope forming ester is dipropylene glycol methyl ether acetate.

* * * * *